US007798953B1

(12) United States Patent
Wilk

(10) Patent No.: US 7,798,953 B1
(45) Date of Patent: Sep. 21, 2010

(54) METHOD AND DEVICE FOR IMPROVING CARDIAC FUNCTION

(75) Inventor: Peter J. Wilk, New York, NY (US)

(73) Assignee: Wilk Patent, LLC, New York, NY (US)

( * ) Notice: Subject to any disclaimer, the term of this patent is extended or adjusted under 35 U.S.C. 154(b) by 522 days.

(21) Appl. No.: 11/649,661

(22) Filed: Jan. 3, 2007

Related U.S. Application Data

(60) Provisional application No. 60/756,005, filed on Jan. 4, 2006.

(51) Int. Cl.
*A61B 1/00* (2006.01)
(52) U.S. Cl. ......................................................... 600/16
(58) Field of Classification Search ............. 600/16–18; 607/122
See application file for complete search history.

(56) References Cited

U.S. PATENT DOCUMENTS

| 6,068,638 | A | 5/2000 | Makower | |
| 6,776,754 | B1 * | 8/2004 | Wilk | ............................ 600/16 |
| 2004/0186546 | A1 * | 9/2004 | Mandrusov et al. | ......... 607/122 |
| 2005/0177228 | A1 * | 8/2005 | Solem et al. | ............... 623/2.36 |

* cited by examiner

*Primary Examiner*—George R Evanisko
*Assistant Examiner*—Rex Holmes
(74) *Attorney, Agent, or Firm*—R. Neil Sudol; Henry D. Coleman; William J. Sapone

(57) ABSTRACT

In a method for improving cardiac performance, a compressive cardiac implant is passed through an anterior intraventricular vein of a patient's heart to a position proximate an apex or lower end of a left ventricle of the patient's heart. A distal end portion of the compressive cardiac implant is moved from the anterior intraventricular vein into the patient's left ventricle and thereafter passed through a septum of the patient's heart and into a right ventricle thereof. The distal end portion of the compressive cardiac implant is then engaged with the septum, and the compressive cardiac implant is operated to compress the apex or lower end of the patient's left ventricle so as to reduce the effective volume of the left ventricle.

7 Claims, 5 Drawing Sheets

METHOD AND DEVICE FOR IMPROVING CARDIAC FUNCTION

CROSS-REFERENCE TO RELATED APPLICATION

This application claims the benefit of U.S. Provisional Patent Application No. 60/756,005 filed Jan. 4, 2006.

BACKGROUND OF THE INVENTION

This invention relates to a method and device for improving cardiac function, particularly where there is congestive heart failure.

Congestive heart failure occurs, inter alia, where there has been a heart attack or an infection. In either case, the pumping action of the heart is impaired. In another malfunction, left ventricular hypertrophy, the myocardium of the left ventricle becomes thickened to the point of interfering with effective heart contraction.

A surgical procedure for treating congestive heart failure involves inserting cardiac implant into a patient for purposes of constricting or closing off a lower, apical, portion of at least one ventricle of the patient's heart, thereby reducing ventricular volume and enhancing pumping efficiency.

This treatment of congestive heart failure may be implemented via minimally invasive procedures. Such procedures are described in several of the following patents on this technique: U.S. Pat. No. 6,155,968, U.S. Pat. No. 6,258,021, U.S. Pat. No. 6,776,754, and U.S. Pat. No. 6,572,529, as well as U.S. patent application Ser. No. 09/435,525, filed Nov. 8, 1999, now U.S. Pat. No. 6,514,077, and U.S. patent application Ser. No. 10/886,177 filed Jul. 7, 2004.

OBJECTS OF THE INVENTION

An object of the present invention is to provide an improved surgical method for treating congestive heart failure.

It is another object of the present invention to provide a surgical method for treating congestive heart failure which may be used to facilitate minimally invasive procedures.

These and other objects of the present invention will be apparent from the drawings and descriptions herein. Although every object of the invention is believed to be attained by at least one embodiment of the invention, there is not necessarily any single embodiment that achieves all of the objects of the invention.

SUMMARY OF THE INVENTION

A method for improving cardiac performance comprises, in accordance with the present invention, (a) passing a compressive cardiac implant through an anterior intraventricular vein of a patient's heart to a position proximate an apex or lower end of a left ventricle of the patient's heart, (b) subsequently moving a distal end portion of the compressive cardiac implant from the anterior intraventricular vein into the patient's left ventricle, (c) thereafter passing the distal end portion of the compressive cardiac implant through a septum of the patient's heart and into a right ventricle thereof, (d) engaging the distal end portion of the compressive cardiac implant with the septum, and (e) operating the compressive cardiac implant to compress the apex or lower end of the patient's left ventricle so as to reduce the effective volume of the left ventricle.

The engaging of the distal end portion of the compressive cardiac implant with the septum may include reconfiguring the distal end portion from a collapsed insertion configuration to an expanded configuration and drawing the expanded distal end portion of the compressive cardiac implant into contact with the patient's cardiac septum.

The operating of the compressive cardiac implant may additionally include engaging a proximal end portion of the compressive cardiac implant in the patient's heart tissues on a side of the patient's left ventricle opposite the septum. Moreover, the operating of the compressive cardiac implant may further include placing tension on a shaft of the compressive cardiac implant connecting the distal end portion and the proximal end portion.

Prior to the passing of the compressive cardiac implant through an anterior intraventricular vein, the compressive cardiac implant is passed through the patient's vena cava and right atrium and into the patient's anterior intraventricular vein.

It is contemplated that the compressive cardiac implant is passed through the patient's vena cava and right atrium and into the patient's anterior intraventricular vein and then through or along the anterior intraventricular vein by moving the implant device inside a catheter. The catheter is deployed to extend through the vena cava, right atrium and anterior intraventricular vein.

The catheter is removed from the patient and particularly from the patient's anterior intraventricular vein after the deployment (operating) of the compressive cardiac implant.

DEFINITIONS

The term "clamping device" is used herein to denote a device that is inserted into a patient and placed in contact with the patient's heart to exert a compressive or constrictive force on the heart. In the context of the present invention the purpose of a clamping device is to constrict or reduce ventricular volume to facilitate cardiac function. A clamping or compressive device as used in the present method may be a tensile member such as a tack, pin, wire, etc., that experience an increase in tensile stress during application of the clamping or compressive device to a patient's heart.

The term "transmitter" or "communications componentry" is used herein to denote generally components for communicating a stress measurement to a user. The transmitter includes components that transmit an electrical signal from a sensor to an indicator, gauge, alert signal generator or other means for advising a user or operator such as a surgeon, radiologist, or other medical specialist as to a detected stress level or magnitude. A transmitter may include a wireless communications link or a hard wire link. The transmitter may also incorporate a specially programmed generally purpose computer or microprocessor or a hard wired logic circuit. The transmitter may include an electro-optical transducer such as an LCD display, an electro-acoustic transducer such as a piezoelectric speaker, or an electromechanical transducer such as a vibrator for communicating a detected result via a tactile signal.

DETAILED DESCRIPTION

Figure 1:
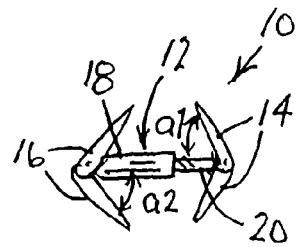
FIG. 1 is a schematic side elevational view of a clamping or constriction device utilizable in a method in accordance with the present invention, the clamping device being shown in an opened or expanded configuration.
Figure 2:
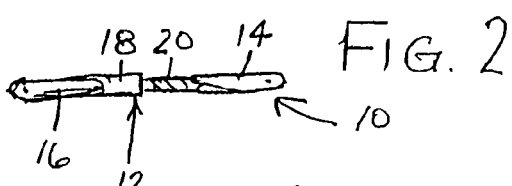
FIG. 2 is a schematic side elevational view of the clamping or constriction device of FIG. 1 in a fully closed transport configuration.
Figure 3:
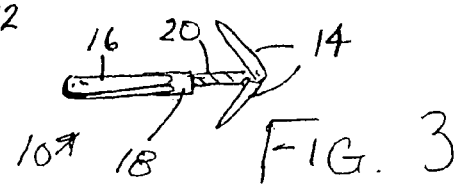
FIG. 3 is a schematic side elevational view of the clamping or constriction device of FIGS. 1 and 2 in a partially opened configuration.

FIGS. 1-3 illustrate a clamping device 10 for applying compressive force to a lower or apical portion of a patient's heart for purposes of reducing ventricular volume in the treatment of congestive heart failure. Clamping device 10 includes a shaft 12 provided at a first end with a first pair of arms or barbs 14 and at a second end with a second pair of arms or barbs 16. Shaft 12 includes an outer tubular member 18 receiving an inner rod or tubular member 20. Arms 14 are pivotably mounted to inner member 20, while arms 16 are pivotably mounted to outer tubular member 18. Arms 16 and 16 are spring biased to assume an angled opened configuration shown in FIG. 1. In the configuration, arms 14 and 16 are inclined toward each other at acute angles a1 and a2 with respect to shaft 12.

Figure 4A:
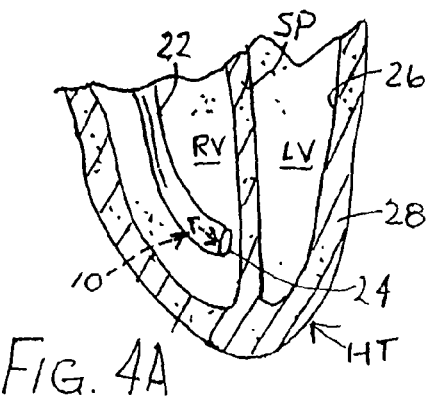
FIGS. 4A-4F are schematic partial cross-sectional views of a heart, showing successive stages in one method of deploying and implanting the clamping device of FIGS. 1-3.
Figure 4B:
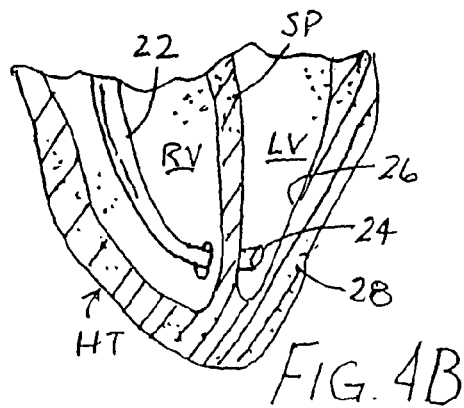

FIGS. 2 and 4A show clamping device 10 in a fully closed configuration in which the clamping device is disposed inside the distal end of a steerable deployment catheter 22. During a deployment and implantation operation, a distal end portion (not separately enumerated) of catheter 22 is guided through the patient's vascular system and into the patient's heart HT, for instance, into the right ventricle RV, as shown in FIG. 4A. The distal tip 24 of catheter 22 is directed to the base of the patient's septum SP where the catheter is pushed through the cardiac tissues and into the left ventricle LV, as shown in FIG. 4B. To that end, distal tip 24 of catheter 22 may be provide with a cauterization ring (not shown) for conducting a cutting and cauterizing current into selected cardiac tissues during the deployment and implantation operation.

Figure 4C:
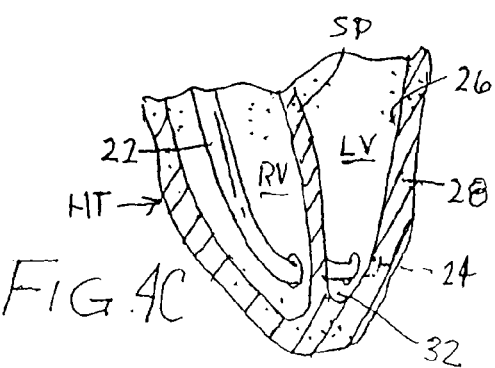
Figure 4D:
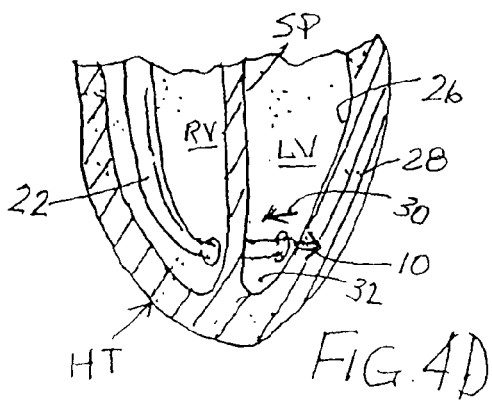

Subsequently, as shown in FIG. 4C, catheter 22 is maneuvered (from outside the patient) to place distal tip 24 in contact with a surface 26 of an outer wall 28 of the patient's heart HT and partially into wall 28. Then clamping device 10 is partially ejected from catheter 22, whereupon arms or barbs 14 spring open, as depicted in FIG. 4D. Catheter 22, with clamping device 10 connected thereto (or more precisely to a deployment wire or rod inside the catheter), is then drawn back in the proximal direction, as indicated by an arrow 30. Arms or barbs 14 become embedded in the tissues or myocardium of outer wall 28 and consequently entrain the outer wall and pull it towards septum SP.

Figure 4E:
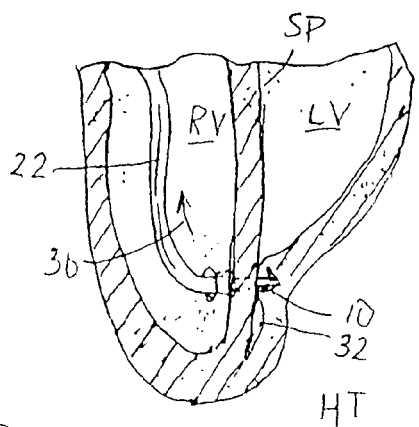
Figure 4F:
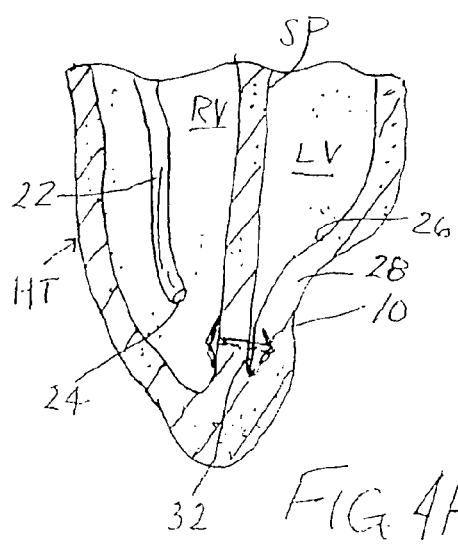

This drawing of catheter 22 in the proximal direction (towards the operating physician) continues until surface 26 of outer heart wall 28 is brought into contact with the inner heart wall or septum SP, as illustrated in FIG. 4E, thereby closing off a lower or apical portion 32 of the left ventricle LV. Clamping device 10 is fully ejected from catheter 22 during the course of this closure operation, so that arms or barbs 16 come into contact with septum SP in the right ventricle RV. Upon a satisfactory closure of lower or apical portion 32, clamping device is separated from the deployment device, as shown in FIG. 4F. Clamping device 10 remains implanted in the patient's heart HT and catheter 232 is withdrawn.

Figure 5:
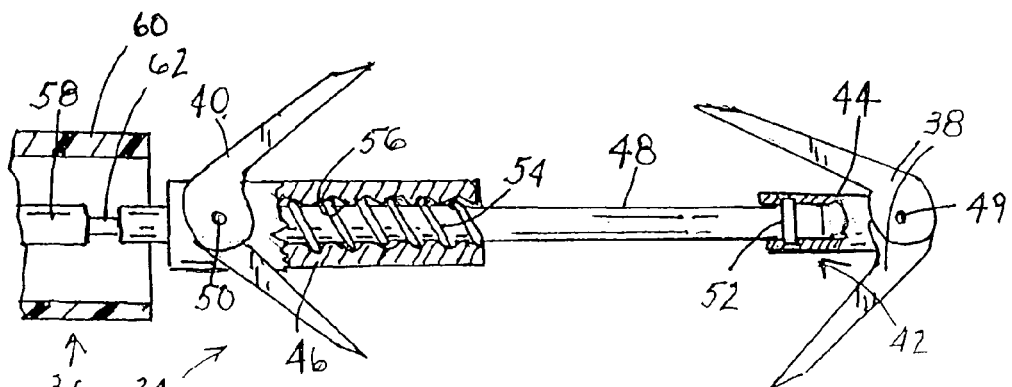
FIG. 5 is a schematic side elevational view, partly in cross-section, of a particular embodiment of the clamping device of FIGS. 1-3.

FIG. 5 depicts a clamping device 34 and a deployment assembly 36 that are utilizable in the method of FIGS. 4A-4F. Clamping device 34 includes two pairs of barbs spring-loaded arms or fingers 38 and 40 that are disposed in spaced relation along a multi-part shaft 42. Shaft 42 includes a pair of sleeves 44 and 46 traversed at least in part by a rod 48. Arms 38 are hingedly attached to sleeve 44 by a first pivot pin 49, while arms 40 are pivotably or swingably coupled to sleeve 46 by a second pivot pin 50.

At one end, rod 48 is provided with an annular bead or flange 52 that is seated in an annular recess or groove (not separately designed) inside sleeve 44, whereby rod 48 is able to rotate with respect to sleeve 44. Rod 48 is additionally provided with an external screw thread 54 that engages an internal screw thread 56 on sleeve 46. Accordingly, a rotation of rod 48 moves sleeve 46 towards sleeve 44, thereby reducing the distance between arms 38 and 40. Thus, the compressive force exerted on septum SP and outer wall 28 by clamping device 34 may be increased to a desirable magnitude, ensuring a suitable constriction and closure of apical portion 32 of heart HT. It is to be noted that arms 40 may be connected to sleeve 46 by a rotational coupling to allow a fixation of arms or barbs 40 relative to septum SP, while still permitting a tightening of the clamping device 34.

Deployment assembly 36 includes a flexible force-transmitting rod or wire 58 that extends longitudinally through a deployment catheter or introducer sheath 60 and is connected to a proximal end of rod 48 via a frangible coupling 62. Coupling 62 is designed to fracture and thereby release clamping device 34 upon the attainment of a predetermined resistance level in further screwing of rod 48 and sleeve 46. In other words, coupling 62 fractures or fails when the torsional stress required to further rotate rod 48 reaches a predetermined magnitude. This magnitude corresponds to a desired degree of compression placed upon septum and outer wall 28 via clamping device 34.

Figure 6:
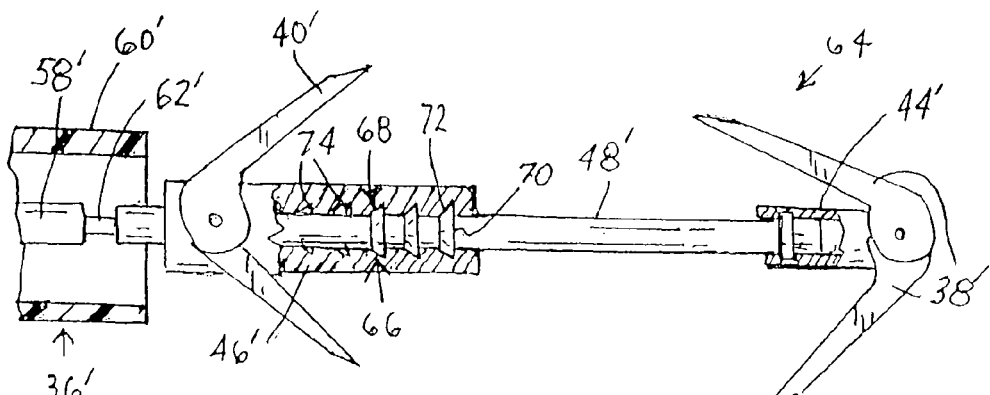
FIG. 6 is a schematic side elevational view, partly in cross-section, of another embodiment of the clamping device of FIGS. 1-3.

FIG. 6 depicts a clamping device 64 that is a modification of the device of FIG. 5. Instead of a screw mechanism, clamping device 64 includes a ratchet mechanism 66 wherein a rod 48' is provided with one or more annular flanges 68 each having a flat transverse surface 70 on a distal side, facing a sleeve 44' and arms 38', and a conically tapered surface 72 on a distal side, facing away from sleeve 44' and arms 38'. Flanges 68 are received in corresponding shaped annular recesses 74 formed inside a sleeve 46'.

It is to be noted that in clamping device 64, sleeve 44' may be rigidly secured to rod 48', since there is not necessarily any rotation or translation of rod 48' relative to sleeve 44'.

In the embodiment of FIG. 6, rod 48' is connected to a deployment assembly 36' including a flexible force-transmitting rod or wire 58' that extends longitudinally through a deployment catheter or introducer sheath 60' and is connected to a proximal end of rod 48' via a frangible coupling 62'. Coupling 62' is designed to fracture and thereby release clamping device 64 upon the attainment of a predetermined resistance to further tightening of the clamping device and more particularly upon attainment of a predetermined tension or longitudinal stress in the coupling member 62'. Thus, coupling 62' fractures or fails when the tensile stress required to pull rod 48' further in a proximal direction relative to sleeve 46' reaches a predetermined magnitude. This magnitude corresponds to a desired degree of compression placed upon septum and outer wall 28 via clamping device 64. Thus, the compressive force exerted on septum SP and outer wall 28 by clamping device 64 automatically assumes a predetermined desired magnitude, ensuring a suitable constriction and closure of apical portion 32 of heart HT. It is to be noted that arms 40' need not be connected to sleeve 46' by a rotational coupling to allow a fixation of arms or barbs 40' relative to septum SP, while still permitting a tightening of the clamping device 64.

The fracture or failure of coupling 62 or 62' causes a separation of rod 58 or 58' from rod 48 or 48', thereby dissociating clamping device 34 or 64 from deployment device 36 or 36' and enabling a withdrawal of the deployment device from the patient.

Figure 7:
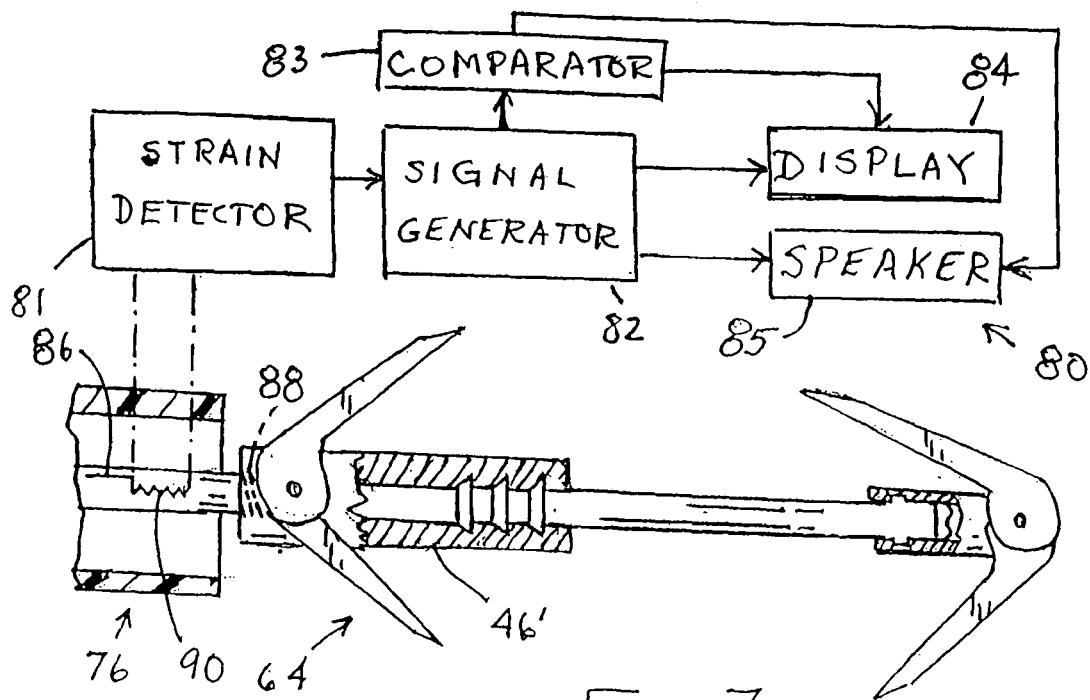
FIG. 7 is a schematic side elevational view, partly in cross-section, of a further embodiment of the clamping device of FIGS. 1-3.
Figure 8:
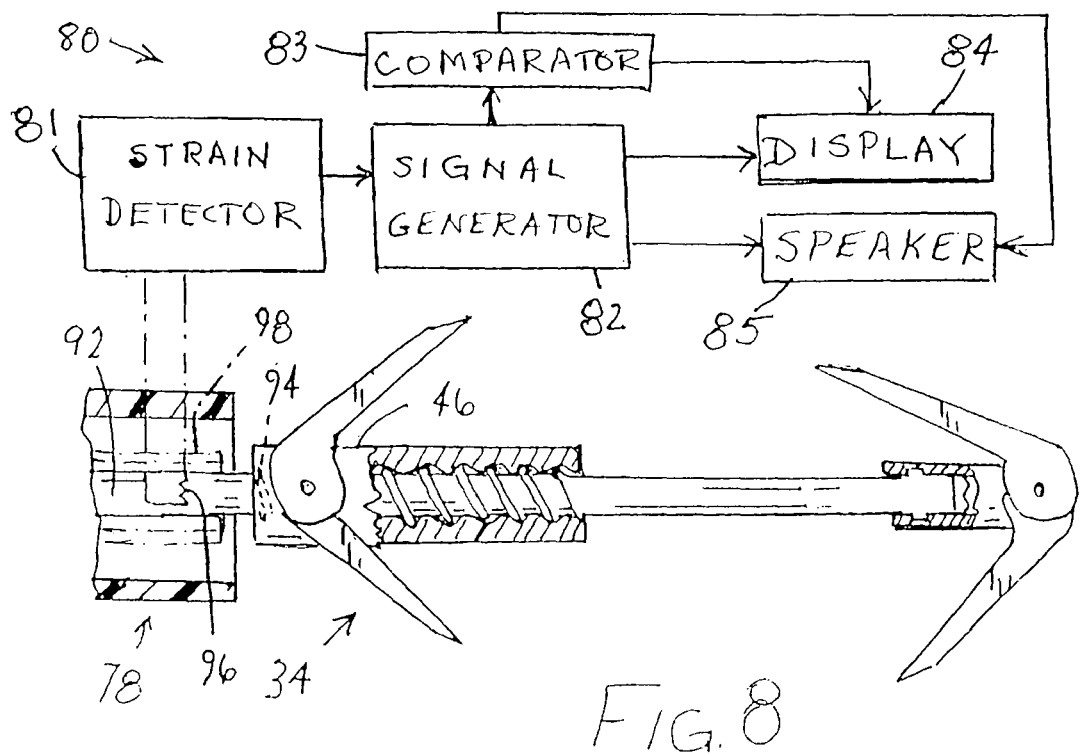
FIG. 8 is a schematic side elevational view, partly in cross-section, of yet another embodiment of the clamping device of FIGS. 1-3.

FIGS. 7 and 8 show clamping devices 64 and 34 of FIGS. 6 and 5, respectively. In the embodiments of FIGS. 7 and 8, clamping devices 64 and 34 are inserted and operated via respective deployment assemblies 76 and 78 in which dissociation of clamping device 64 and 34 from the respective deployment assemblies 76 and 78 is effectuated by an operating physician in response to feedback provided via a monitoring system 80. Monitoring system 80 includes a strain or stress detector 81, a signal generator 82, a comparator 83, an electro-optical transducer assembly such as a display 84, and an electro-acoustic transducer such as a speaker 85.

In the embodiment of FIG. 7, deployment assembly 76 includes a wire or rod member 86 that is connected to sleeve 46' via a screw coupling 88. The tensile stress experienced by rod member 86 during the closure or constriction of clamping device 64 is continuously measured or sensed in real time via a strain gauge resistance wire 90 and strain detector 81 connected thereto. Strain gauge wire 90 provides to signal generator 82 an analog or digital signal that encodes a magnitude proportional to the tensile stress experienced by rod member 82. Signal generator 82 processes the incoming signal and in response thereto induces display 84 to communicate to the user a numerical measure of the degree of compression exerted by clamping device 64 on the cardiac tissues. Alternatively or additionally, signal generator 82 may cause the production of an audio indication of compression level via speaker 85. In that case, signal generator 82 may include voice synthesis components. Comparator 83 optionally induces the generation of a visual alert signal via display 84 or an aural alert signal via speaker 85.

In the embodiment of FIG. 8, deployment assembly 78 includes a wire or rod member 92 that is connected to sleeve 46 via a friction or snap-lock coupling 94. The torsional stress experienced by rod member 92 during the closure or constriction of clamping device 34 is continuously sensed in real time via a strain gauge resistance wire 96 and strain detector 81. The operation of monitoring system 80 in the embodiment of FIG. 8 is substantially similar to the operation of that system in the embodiment of FIG. 7.

In using the embodiments of FIGS. 7 and 8, the operating physician stops further constriction or shortening of clamping devices 64 and 34 upon detecting via monitoring system 80 that the degree of compressive force exerted by the clamping device has reached a desired magnitude. In the embodiment of FIG. 7, the operating physician unscrews rod member 82 from clamping device 64. In the embodiment of FIG. 8, a removal catheter 98 may be placed against a proximal side of sleeve 46' to hold the clamping device 64 in place, while rod member 92 is pulled in the proximal direction.

Figure 9A:
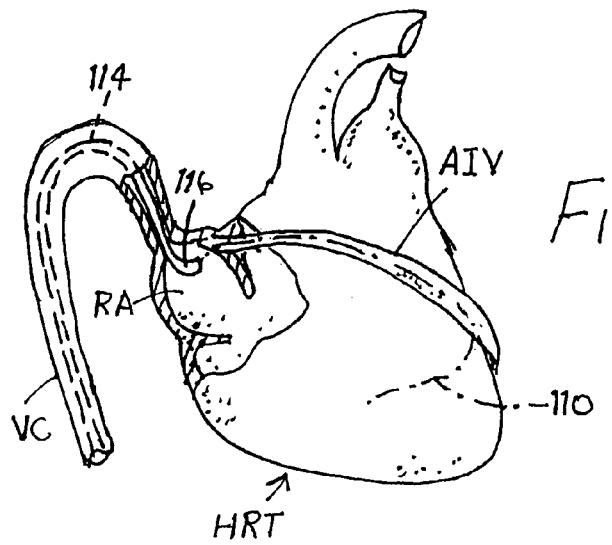
FIGS. 9A-9G are schematic views of a human heart, showing different steps in a cardiac treatment procedure in accordance with the present invention, that may utilize the clamping device shown in FIGS. 1-3 and/or FIGS. 5-8.

As depicted in FIG. 9A, a guide wire 110 is threaded through a patient's vascular system and particularly through the patient's vena cava VC to the patient's heart HRT. Guide wire 110 is passed through the patient's right atrium RA and from there into the anterior intraventricular vein AIV. Wire 110 is then passed along the anterior intraventricular vein AIV to a position 112 proximate a lower end or apex of the patient's left ventricle LV. The distal end (not separately designated) of the guide wire 110 is then turned and inserted through the wall of the anterior intraventricular vein AIV into the left ventricle LV. Further movement of the guide wire in the distal direction brings the distal tip of the wire through the patient's cardiac septum CS and into the right ventricle RV.

Figure 9B:
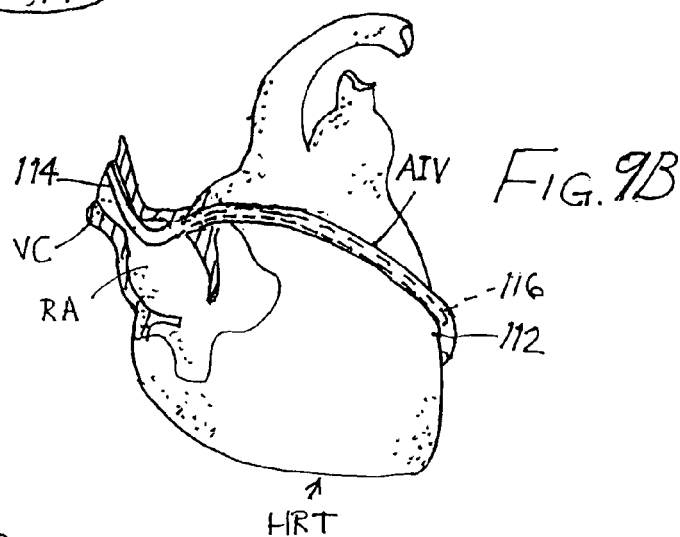
Figure 9C:
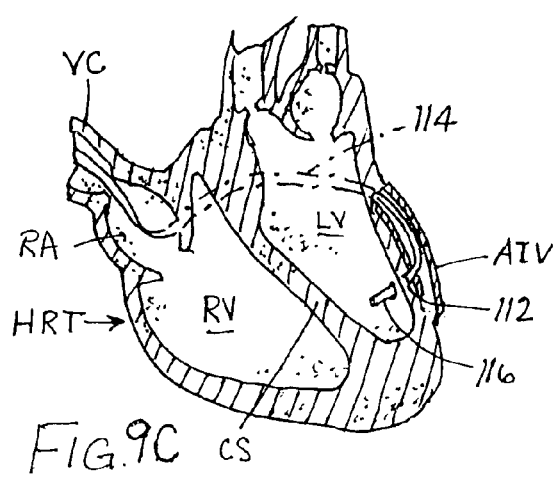
Figure 9D:
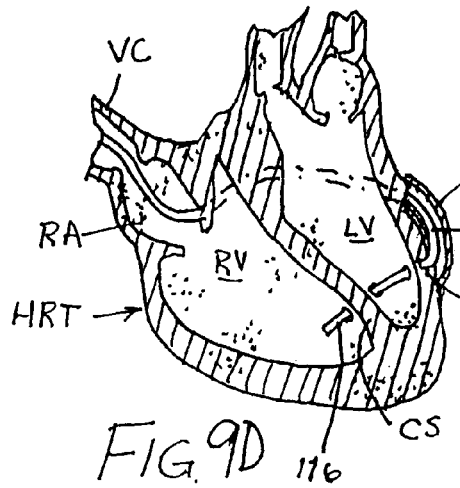

Subsequently, a catheter 114 is inserted over guide wire 110. A distal end portion 116 of catheter 114 follows the same path as the guide wire, that is, along the vena cava VC into the right atrium RA (FIG. 9A), along the anterior intraventricular vein AIV to the position 112 proximate the lower end or apex of the left ventricle LV (FIG. 9B), into the left ventricle LV (FIG. 9C), and through the septum CS and into the right ventricle RV (FIG. 9D).

After the completed insertion of catheter 114, guide wire 110 is removed, while leaving the catheter in place along the above-described deployment path. A compressive cardiac implant 118 (FIGS. 9E-9G only) is then inserted through catheter 114. Implant 118 is obviously constrained to follow the deployment path of catheter 114. Thus, implant device 118 moves through the vena cava VC into the right atrium RA (FIG. 9A), along the anterior intraventricular vein AIV to the position 112 proximate the lower end or apex of the left ventricle LV (FIG. 9B), into the left ventricle LV (FIG. 9C), and through the septum CS and into the right ventricle RV (FIG. 9D).

Figure 9E:
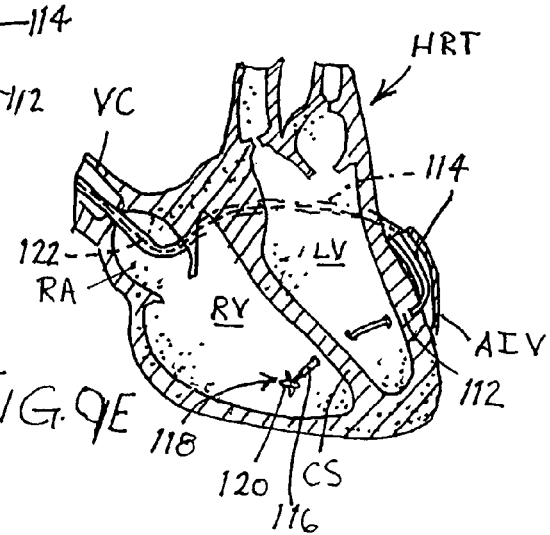
Figure 9F:
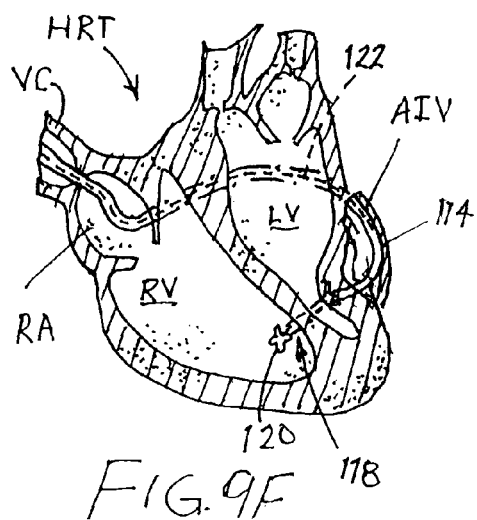
Figure 9G:
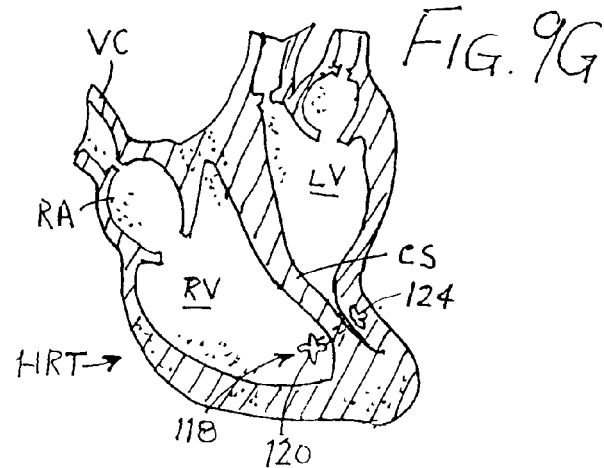

A distal end portion 120 of implant device 118 is then ejected from the distal end portion 116 of catheter 114 into the patient's right ventricle RV. As shown in FIG. 9E, a a contact or anchor element 120 constituting a distal end portion of implant device 118 is then reconfigured or expanded from a collapsed insertion configuration. Thereafter, a tensile force is placed on implant device 118 via a deployment shaft 122 extending through catheter 114, causing expanded anchor element 120 to engage the septum CS and compress the lower or apical end of the left ventricle LV, as depicted in FIG. 9F. Typically, the tensile force implementing the cardiac compression is applied after a contact or anchor element 124 is deployed to engage myocardial tissues proximate to position 112, that is, on a side of the left ventricle LV opposite the septum CS. Compression continues preferably, but not necessarily, until the lower or apical end of the left ventricle LV is entirely closed off, that is, until the septum CS comes into contact with the outer wall of the left ventricle, as illustrated in FIG. 9G. At that juncture, implant device 118 is released from deployment shaft 122, which is then removed from the patient, together with catheter 114.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A method for improving cardiac performance, comprising:
   passing a compressive cardiac implant through an anterior intraventricular vein of a patient's heart to a position proximate an apex or lower end of a left ventricle of the patient's heart;
   subsequently moving a distal end portion of said compressive cardiac implant from the anterior intraventricular vein into the patient's left ventricle;
   thereafter passing said distal end portion of said compressive cardiac implant through a septum of the patient's heart and into a right ventricle thereof;
   engaging said distal end portion of said compressive cardiac implant with said septum; and
   operating said compressive cardiac implant to compress the apex or lower end of the patient's left ventricle so as to reduce the effective volume of the left ventricle.

2. The method defined in claim 1 wherein the engaging of said distal end portion of said compressive cardiac implant includes reconfiguring said distal end portion from a collapsed insertion configuration to an expanded configuration and drawing the expanded distal end portion of said compressive cardiac implant into contact with the patient's cardiac septum.

3. The method defined in claim 2 wherein the operating of said compressive cardiac implant includes engaging a proximal end portion of said compressive cardiac implant in the patient's heart tissues on a side of the patient's left ventricle opposite the septum.

4. The method defined in claim 3 wherein the operating of said compressive cardiac implant further includes placing tension on a shaft of said compressive cardiac implant connecting said distal end portion and said proximal end portion.

5. The method defined in claim 1, further comprising, prior to the passing of said compressive cardiac implant through an anterior intraventricular vein, passing said compressive cardiac implant through the patient's vena cava and right atrium and into the patient's anterior intraventricular vein.

6. The method defined in claim 5 wherein the passing of said compressive cardiac implant through the patient's vena cava and right atrium and into the patient's anterior intraventricular vein and the passing of said compressive cardiac implant through the patient's anterior intraventricular vein comprises moving said compressive cardiac implant while said compressive cardiac implant is disposed inside a catheter in the vena cava, right atrium and anterior intraventricular vein.

7. The method defined in claim 6, further comprising removing said catheter from the patient's anterior intraventricular vein after the operating of said compressive cardiac implant.

* * * * *